(12) United States Patent
Jagelski et al.

(10) Patent No.: US 12,070,227 B2
(45) Date of Patent: Aug. 27, 2024

(54) MEDICAL DEVICE INCLUDING A HEMOSTATIS CLIP

(71) Applicant: BOSTON SCIENTIFIC SCIMED INC., Maple Grove, MN (US)

(72) Inventors: Matthew Robert Jagelski, Marlborough, MA (US); Ryan Evers, Billerica, MA (US); Shawn Ryan, Littleton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 211 days.

(21) Appl. No.: 17/715,908

(22) Filed: Apr. 7, 2022

(65) Prior Publication Data

US 2022/0323080 A1 Oct. 13, 2022

Related U.S. Application Data

(60) Provisional application No. 63/171,748, filed on Apr. 7, 2021.

(51) Int. Cl.
*A61B 17/128* (2006.01)
*A61B 17/122* (2006.01)
*A61B 17/12* (2006.01)

(52) U.S. Cl.
CPC ...... *A61B 17/1285* (2013.01); *A61B 17/1227* (2013.01); *A61B 2017/12004* (2013.01)

(58) Field of Classification Search
CPC .............. A61B 17/1227; A61B 17/128; A61B 17/1285; A61B 2017/12004
See application file for complete search history.

(56) References Cited

U.S. PATENT DOCUMENTS

| | | | |
|---|---|---|---|
| 6,808,491 B2 | 10/2004 | Kortenbach et al. | |
| 6,911,032 B2* | 6/2005 | Jugenheimer | ...... A61B 17/1285 600/104 |
| 7,488,334 B2* | 2/2009 | Jugenheimer | ........ A61B 17/128 606/142 |
| 7,828,811 B2* | 11/2010 | Kortenbach | ........... A61B 10/06 606/205 |
| 8,043,307 B2* | 10/2011 | Jugenheimer | ...... A61B 17/1285 606/139 |
| 8,062,311 B2* | 11/2011 | Litscher | ............... A61B 17/122 606/143 |

(Continued)

FOREIGN PATENT DOCUMENTS

WO 2021133740 A1 11/2021

OTHER PUBLICATIONS

International Search Report and Written Opinion dated Jul. 28, 2022 for International Application No. PCT/US2022/023929.

*Primary Examiner* — Ryan J. Severson
(74) *Attorney, Agent, or Firm* — Seager, Tufte & Wickhem, LLP

(57) ABSTRACT

An example medical device is disclosed. The example medical device includes a shaft having a proximal end region, a distal end region and an outer surface. The medical device also includes a hemostasis clip coupled to the outer surface of the distal end region of the shaft, wherein the hemostasis clip is configured to shift between an open position and a closed position. Further, the medical device includes a tension member coupled to the hemostasis clip, wherein actuation of the tension member shifts the hemostasis clip between the open position and the closed position.

20 Claims, 15 Drawing Sheets

(56) References Cited

U.S. PATENT DOCUMENTS

| | | | |
|---|---|---|---|
| 8,679,136 B2 | 3/2014 | Mitelberg | |
| 8,784,436 B2 | 7/2014 | Ho et al. | |
| 9,044,240 B2* | 6/2015 | Weitzner | A61B 17/1285 |
| 9,370,369 B2 | 6/2016 | Size et al. | |
| 11,540,697 B2* | 1/2023 | Schurr | A61B 17/1227 |
| 2002/0062130 A1* | 5/2002 | Jugenheimer | A61B 17/1285 |
| | | | 606/142 |
| 2002/0173786 A1* | 11/2002 | Kortenbach | A61B 10/06 |
| | | | 606/49 |
| 2005/0107809 A1* | 5/2005 | Litscher | A61B 17/1285 |
| | | | 606/142 |
| 2005/0182426 A1* | 8/2005 | Adams | A61B 17/122 |
| | | | 606/213 |
| 2008/0207995 A1* | 8/2008 | Kortenbach | A61B 18/1445 |
| | | | 600/104 |
| 2011/0152888 A1* | 6/2011 | Ho | A61B 1/00087 |
| | | | 606/151 |
| 2011/0245855 A1* | 10/2011 | Matsuoka | A61B 17/122 |
| | | | 606/157 |
| 2012/0149979 A1* | 6/2012 | Mitelberg | A61B 1/018 |
| | | | 600/106 |
| 2014/0228864 A1* | 8/2014 | Jugenheimer | A61B 17/122 |
| | | | 606/157 |
| 2021/0052141 A1 | 2/2021 | Schurr et al. | |
| 2022/0323080 A1* | 10/2022 | Jagelski | A61B 17/1285 |

* cited by examiner

MEDICAL DEVICE INCLUDING A HEMOSTATIS CLIP

CROSS REFERENCE TO RELATED APPLICATIONS

This application claims the benefit of and priority to U.S. Provisional Patent Application Ser. No. 63/171,748 filed on Apr. 7, 2021, the disclosure of which is incorporated herein by reference.

TECHNICAL FIELD

The present disclosure pertains to medical devices, and methods for manufacturing medical devices. More particularly, the present disclosure pertains to hemostasis clips connected with other structures, and methods for manufacturing and using such devices.

BACKGROUND

A wide variety of intracorporeal medical devices have been developed for medical use, for example, intravascular use. Some of these devices include catheters, endoscopes, hemostasis clips (e.g., tissue closure devices), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a shaft having a proximal end region, a distal end region and an outer surface. The medical device also includes a hemostasis clip coupled to the outer surface of the distal end region of the shaft, wherein the hemostasis clip is configured to shift between an open position and a closed position. Further, the medical device includes a tension member coupled to the hemostasis clip, wherein actuation of the tension member shifts the hemostasis clip between the open position and the closed position.

Alternatively or additionally to any of the embodiments above, wherein the hemostasis clip includes an upper jaw pivotable to a lower jaw, and wherein the tension member is coupled to a portion of the upper jaw.

Alternatively or additionally to any of the embodiments above, wherein the upper jaw includes and aperture, and wherein the tension member extends through the aperture.

Alternatively or additionally to any of the embodiments above, further comprising a shear member, and wherein the shear member is coupled to the upper jaw, the tension member, or both the upper jaw and the tension member.

Alternatively or additionally to any of the embodiments above, wherein the shear member is coupled to the tension member at a welded connection, and wherein moving the shear member relative to the tension member severs the welded connection to separate the tension member from the shear member.

Alternatively or additionally to any of the embodiments above, wherein a rivet couples the shear member to the tension member, and wherein moving the shear member relative to the tension member severs the rivet to separate the tension member from the shear member.

Alternatively or additionally to any of the embodiments above, wherein the lower jaw is held in fixed position relative to the upper jaw as the upper jaw is pivoted relative to the lower jaw.

Alternatively or additionally to any of the embodiments above, further comprising a cap disposed along the distal end region of the shaft, and wherein in the hemostasis clip is releasably attached to an outer surface of the cap.

Alternatively or additionally to any of the embodiments above, wherein the cap includes a first projection, and wherein the hemostasis clip includes a curved portion configured to engage the first projection.

Alternatively or additionally to any of the embodiments above, wherein a portion of the shear member engages a portion of the first projection.

Alternatively or additionally to any of the embodiments above, wherein the cap includes a connection member configured to translate from a first position to a second position, and wherein shifting the connection member from the first position to the second position releases the hemostasis clip from the cap.

Alternatively or additionally to any of the embodiments above, further comprising a release member coupled to the connection member, and wherein retracting the release member translates the connection member from the first position to the second position.

An example endoscope includes a handle, a shaft coupled to the handle, the shaft having a proximal end region, a distal end region and an outer surface. The endoscope also includes a cap disposed along the distal end region of the shaft, a hemostasis clip releasably attached to an outer surface of the cap, wherein the hemostasis clip is configured to shift between an open position and a closed position. Further, the endoscope also includes a tension member coupled to the hemostasis clip, wherein actuation of the tension member shifts the hemostasis clip between the open position and the closed position.

Alternatively or additionally to any of the embodiments above, wherein the hemostasis clip includes an upper jaw pivotable to a lower jaw, and wherein the tension member is coupled to a portion of the upper jaw.

Alternatively or additionally to any of the embodiments above, wherein the upper jaw includes and aperture, and wherein the tension member extends through the aperture.

Alternatively or additionally to any of the embodiments above, further comprising a shear member, and wherein the shear member is coupled to the upper jaw, the tension member, or both the upper jaw and the tension member.

Alternatively or additionally to any of the embodiments above, wherein the lower jaw is held in fixed position relative to the upper jaw as the upper jaw is rotated relative to the lower jaw.

Alternatively or additionally to any of the embodiments above, wherein the cap includes a first projection, and wherein the hemostasis clip includes a curved portion configured to engage the first projection.

Alternatively or additionally to any of the embodiments above, wherein the upper jaw pivots relative to the lower jaw about the first projection.

An example method of attaching a hemostasis clip to a target tissue includes advancing an endoscope to the target tissue, wherein the endoscope includes a shaft having a proximal end region, a distal end region and an outer surface. The endoscope also includes a hemostasis clip coupled to the outer surface of the distal end region of the shaft, wherein the hemostasis clip is configured to shift between an open position and a closed position. Further, the endoscope also includes a tension member coupled to the hemostasis clip. The method further includes retracting the tension member to shift the hemostasis clip to the open position, engaging the hemostasis clip with the target tissue and releasing the tension member to shift the hemostasis clip to the closed position.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
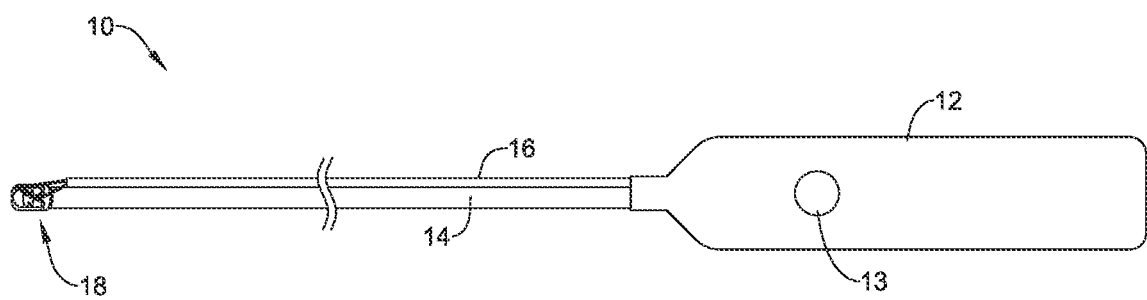
FIG. 1 illustrates an example hemostasis clip delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Pathologies of the body lumens and hollow organs are often treated through endoscopic procedures, many of which may require mechanisms to control bleeding. Tools for deploying hemostatic clips via an endoscope are often used to stop internal bleeding by clamping together the edges of the wounds or incisions. Hemostasis clips (e.g., wound closure devices) may grasp tissue surrounding a wound and hold the edges of the wound together by applying pressure to the target tissue site to allow natural healing processes to close the wound. Specialized endoscopic clipping devices are used to deliver the clips to the desired locations within the body and to position and deploy the clips at the desired locations after which the clip delivery device is withdrawn, leaving the clip within the body. These clips may be left in place until they are removed via natural processes or later through a separate procedure after the bleeding site has healed.

FIG. 1 illustrates an example medical device 10 including a distal end and a proximal end. The medical device 10 may include a shaft 14 having a proximal end region and a distal end region. In some examples, the shaft 14 may include an endoscope, laproscope, catheter, guide tube, or the like. As will be described in greater detail below, the distal end of the medical device 10 may be advanced within a portion of a body lumen to a position adjacent a target tissue, such as a lesion, while the proximal end of the medical device system 10 may extend out of the body lumen to a position outside the body.

FIG. 1 further illustrates that the proximal end region of the shaft 14 may be coupled to a control member 12 (e.g., handle, actuator, etc.). The control member 12 may be utilized as a grip to control the translation of the shaft 14. Further, the control member 12 may also permit a user to rotate the shaft 14. As will be described in greater detail below, the control member 12 may be utilized by a clinician to advance the distal end region of the shaft 14 to a position adjacent a target tissue to perform a medical treatment. Additionally, the control member 12 may include one or more actuators, gears, levers, etc. which allow a clinician to manipulate the shaft 14 in addition to other features components (e.g., wound closure devices) of the medical device 10.

In some examples, the medical device 10 may include additional features. For example, the medical device 10 shown in FIG. 1 may include a hemostasis clip 18 (e.g., a defect closure device) positioned on the distal end region of the shaft 14 (e.g., endoscope). In some examples, such as the example shown in FIG. 1, the hemostasis clip 18 may be disposed along the outer surface of the shaft 14. This type of hemostasis clip may be referred to as an "over-the-scope" clip (e.g., OTSC) as the clip 18 is positioned on the outer surface of the shaft 14 (e.g., endoscope) or other similar medical device.

As will be described in greater detail below, the hemostasis clip 18 may be utilized to seal or occlude a bleeding target tissue site during or after a surgical procedure. For example, if a target tissue is cut during surgery, a hemostasis clip may be utilized to grasp the cut tissue and immediately stop the bleeding. Accordingly, the hemostasis clip may need to be actuated to grasp the tissue and, thereafter, be removed from the medical device 10 and remain attached to the target tissue site until the bleeding has stopped. As will be described in greater detail below, FIG. 1 illustrates an actuation sheath 16 attached to the shaft 14. The actuation sheath 16 may include a lumen through which one or more actuation members (shown in FIG. 2) may extend and couple to the hemostasis clip 18.

Figure 2:
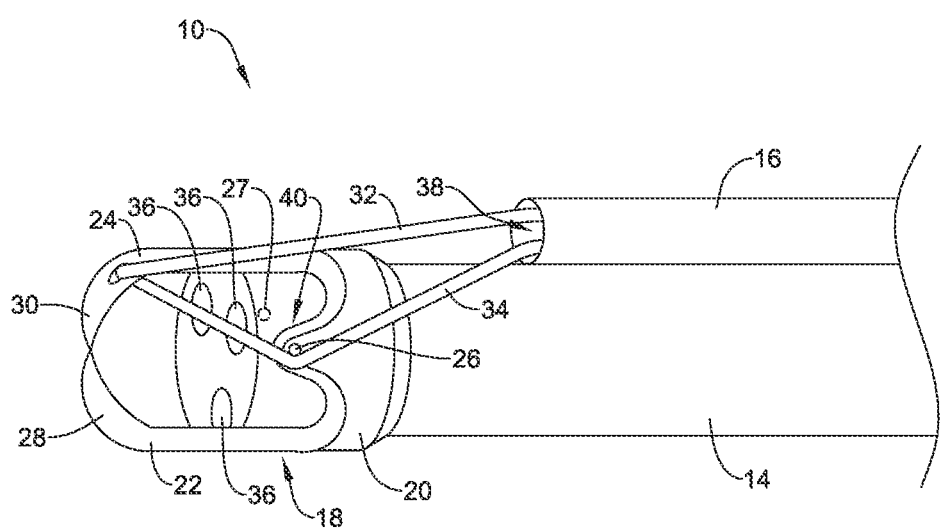
FIG. 2 illustrates the hemostasis clip shown in FIG. 1 in a first position.

FIG. 2 illustrates the distal end of the medical device 10. As shown in FIG. 2, one or more lumens 36 may extend through the shaft 14 from its proximal end region to its the distal end region. In some examples, one or more of the lumens 36 may be referred to as a "working channel" of the medical device 10. The working channel may be designed to permit a variety of medical devices to pass therethrough. For example, a clinician may pass or exchange a variety of medical devices through the working channel 36 over the course of a given medical procedure. The medical devices passed within the working channel 36 may be utilized to treat a tissue target site. It can further be appreciated that the reference numerals 36 may represent a working channel, while the other reference numerals may represent additional working channels of the shaft 14 or they may represent other features (e.g., LED light, water jet, camera, etc.) of the shaft 14 (e.g., endoscope).

Additionally, FIG. 2 illustrates the hemostasis clip 18 positioned on the distal end region of the shaft 14. However, FIG. 2 further illustrates that the shaft 14 may include a cap 20 positioned on the distal end thereof. The cap 20 may be positioned on the outer surface of the shaft 14 and extend around the circumference of the outer surface of the shaft 14. It can be appreciated that, in some examples, the cap 20 may include an outer diameter which is greater than the outer diameter of the shaft 14. Additionally, FIG. 2 illustrates the distal end of the cap may longitudinally aligned with the end of the shaft 14 (e.g., aligned with the end of the endoscope 14).

Figure 9:
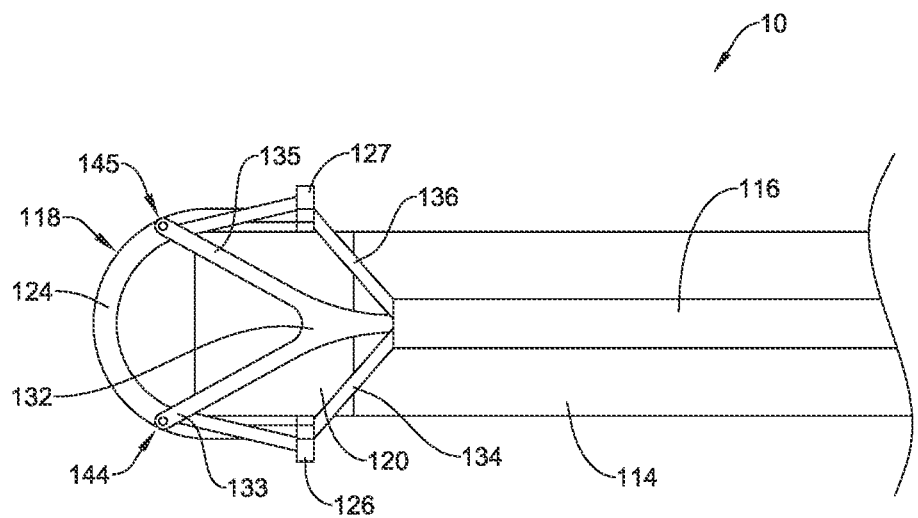
FIG. 9 illustrates another example hemostasis clip delivery system.

FIG. 2 further illustrates that the cap 20 may include one or more projections 26 extending radially outward from an outer surface of the cap 20. It can be appreciated that while FIG. 2 shows a first projection 26 extending radially outward from the outer surface of the cap 20, in some examples, a second projection 27 may be positioned 180 degrees away from the first projection 26 (e.g., on other side of the cap 20), whereby the center region of the first projection 26 and the center region of the second projection 27 may be aligned along a common axis. For example, FIG. 9 illustrates an alternative embodiment of the medical device 10 having a first projection 126 aligned with a second projection 127. The same arrangement may be utilized for the medical device 10 illustrated in FIG. 2.

Figure 4:
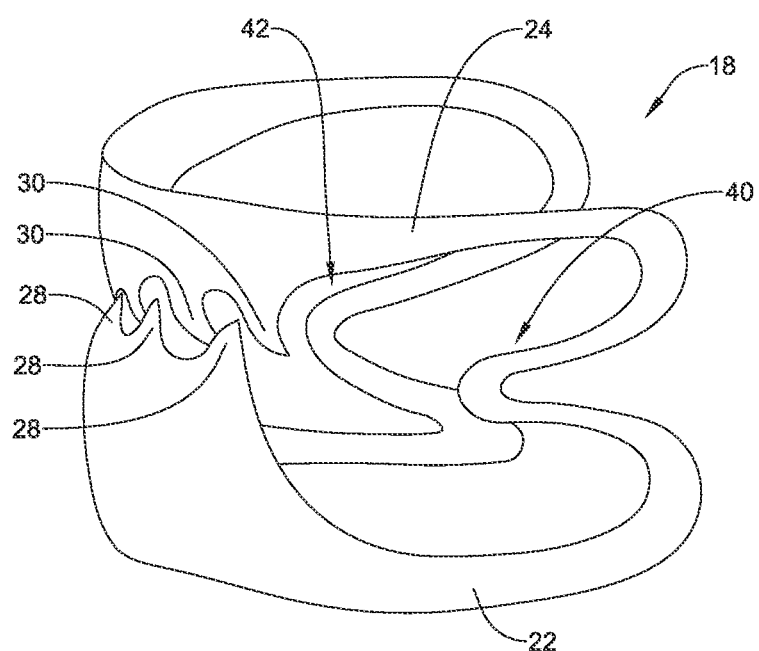
FIG. 4 illustrates an example hemostasis clip.

It can be appreciated from FIG. 2 that, in some examples, the hemostasis clip 18 may positioned along a portion of the cap 20. For example, FIG. 2 illustrates that the hemostasis clip 18 may be positioned on the outer surface of the cap 20. FIG. 2 further illustrates that the hemostasis clip 18 may include an upper jaw 24 and a lower jaw 22 connected to each other via one or more curved (e.g., bent) portions 40. For example, FIG. 4 illustrates that the hemostasis clip 18 may include the first curved portion 40 and a second curved portion 42 (shown in FIG. 4) which connect the upper jaw 24 to the lower jaw 22. As will be described in greater detail below with respect to FIG. 4, the upper jaw 24 of the hemostasis clip 18 may include one or more upper teeth 30, while the lower jaw 22 of the hemostasis clip 18 may include one or more lower teeth 28.

In some examples, the first curved portion 40 may be configured to engage the projection 26 while the second curved portion 42 (shown in FIG. 4) may be configured to engage the second projection 27 of the cap 20. For example, each of the first curved portion 40 and the second curved portion 42 may be shaped to mate with the first projection 26 and the second projection 27 of the cap 20, respectively. Further, it can be appreciated that in some example, the first curved portion 40 and the second curved portion 42 may each be designed to form press fit with the first projection 26 and the second projection 27, respectively. In other words, in some examples, the first curved portion 40 and the second curved portion 42 of the hemostasis clip 18 may be designed to "snap" onto the first projection 26 and the second projection 27 of the cap 20, respectively. The engagement of the first curved portion 40 and the second curved portion 42 of the hemostasis clip 18 may form a releasably secure the hemostasis clip 18 to the cap 20.

FIG. 2 illustrates that the medical device 10 may also include a tension wire 32 and a shear wire 34, each of which may be coupled to the hemostasis clip 18. It can be appreciated that each of the tension wire 32 and the shear wire 34 may extend from the hemostasis clip 18, through the actuation sheath 16 and be coupled to the control member 12 (shown in FIG. 1).

Figure 3:
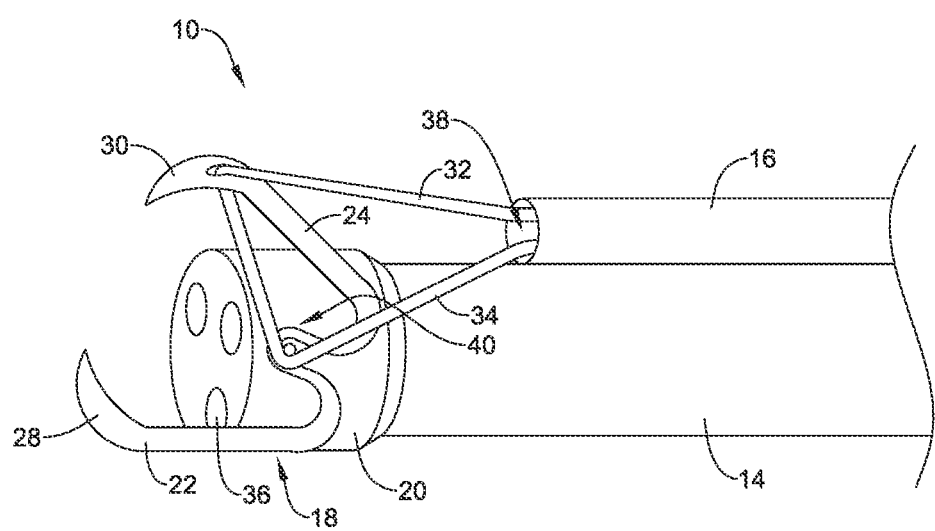
FIG. 3 illustrates the hemostasis clip shown in FIG. 1 in a second position.

As discussed above, the hemostasis clip 18 may be utilized to grasp and occlude tissue as a target tissue site. Therefore, it can be appreciated that the hemostasis clip 18 may be actuated between a first position (e.g., a closed position as shown in FIG. 2) to a second position (e.g., an open position as shown in FIG. 3). It can be further appreciated that to actuate the hemostasis clip 18 between the first position and the second position, the upper jaw 24 may be rotated relative to the lower jaw 22. Accordingly, in some examples, the lower jaw 22 may be held in a fixed position relative to the cap 20, whereby the upper jaw 24 may be rotated relative to the lower jaw 22 (which is being held in a fixed position relative to the cap 20).

It can further be appreciated that to actuate the upper jaw 24 relative to the lower jaw 22, a force may need to be applied to the upper jaw 24 which rotates the upper jaw 24 away from the lower jaw 22. Accordingly, in some examples, the tension member 32 (e.g., a tension wire) may be utilized to provide a force to the upper jaw 24 which rotates the upper jaw relative to the lower jaw 22.

For example, FIG. 3 illustrates that the tension member 32 may be translated in a distal-to-proximal direction through the lumen 38 of the actuation sheath 16. As described above (and will be further described with respect to FIGS. 5-6 below) the tension member 32 may be coupled to the upper jaw 24 of the hemostasis clip 18. Accordingly, translating the tension member 32 in a distal-to-proximal direction may effectively rotate the upper jaw 24 up and away from the lower jaw 22 (which may remain fixed to the cap 20). FIG. 3 further illustrates that the first curved portion 40 and the second curved portion 42 may remain engaged to the first projection 26 and the second projection 27 as the upper jaw 24 rotates with respect to the lower jaw 22. In other words, the first projection 26 and the second projection 27 may act as pivot points for the first curved portion 40 and the second curved portion 42 as the upper jaw 24 rotates relative to the lower jaw 22.

It can be appreciated that the translation of the tension member 32 through the actuation sheath 16 may be performed by one or more actuation components of the control member 12. For example, a clinical may manipulate one or more actuation components of the control member 12 to shift the hemostasis clip 18 between a first (e.g., open) position and the second (e.g., closed) position. In some examples, a clinician may manipulate a control knob 13 (shown in FIG. 1) to shift the hemostasis clip 18 between a first (e.g., open) position and the second (e.g., closed) position. The knob 13 may be rotated in a clockwise or counter-clockwise direction to translate the tension member 32 in either a proximal or distal direction. However, this is not intended to be limiting. Rather, the handle 12 may include a lever, slider, or any other actuation component which actuates the tension member to shift the hemostasis clip 18 between a first (e.g., open) position and the second (e.g., closed) position.

Additionally, it can be appreciated that, in some examples, the upper jaw 24 may be bias to be in the second (e.g., closed) configuration. For example, while at rest, the upper jaw 24 may be bias to be closed relative to the lower jaw 22. This feature may be accomplished by the first curved portion 40 and the second curved portion 42, which may act as spring elements to bias the upper jaw 24 in a closed configuration. Accordingly, after the upper jaw 24 is rotated to an open position via the tension member 32 (as described above), releasing tension member 32 may close the upper jaw 24 relative to the lower jaw 22.

FIG. 3 further illustrates that while the tension member 32 is being translated in a distal-to-proximal direction to rotate the upper jaw 24 relative to the lower jaw 22, the shear member 34 may be advanced in a proximal-to-distal direction out of the lumen 38 of the delivery sheath 16. As discussed above (and will be further described with respect to FIGS. 5-6 below) the shear member 32 may also be coupled to the upper jaw 24 of the hemostasis clip 18 (as will be described below, the shear member 32 may be coupled to both the tension member 32 and the upper jaw 24). Accordingly, as the tension member 32 is being translated in a distal-to-proximal direction to rotate the upper jaw 24 relative to the lower jaw 22, the shear member 34 may be "pulled" (e.g., drawn) out of the lumen 38 as the tension member 32 is translated into the lumen 38. Like that described above with respect to the tension member 32, a clinician may manipulate one or more actuation components of the control member 12 to permit the shear member 34 to be pulled out of the lumen 38 of the actuation sheath 16 as the tension member 32 is pulled into the lumen 38 of the actuation sheath 16. It can be appreciated that, in some examples, a single actuation component on the control member 12 may permit the shear member 34 to be pulled out of the lumen 38 of the actuation sheath 16 coincident with the tension member 32 being pulled into the lumen 38 of the actuation sheath 16.

FIG. 4 illustrates the example hemostasis clip 18 described removed from the medical device 10. As described above, the hemostasis clip 18 may include an upper jaw 24 and a lower jaw 22. The upper jaw 24 may be connected to the lower jaw 22 via a first curved portion 40 and a second curved portion 42. Additionally, FIG. 4 illustrates that the first curved portion 40 and the second curved portion 42 may be shaped to accept the first projection 26 and the second projection 27 of the cap 20, as described above.

FIG. 4 further illustrates that the first curved portion 40 and the second curved portion 42 may be spaced apart from one another to allow the hemostasis clip 18 to be inserted onto the cap 20. For example, it can be appreciated that, prior to tracking the shaft 14 to a target tissue site, the distal end region of the shaft 14 may be inserted between the first curved portion 40 and the second covered portion 42, whereby the hemostasis clip 18 may then be advanced along the outer surface of the cap 20 until the first projection 26 and the second projection 27 engage the first curved portion 40 and the second curved portion 42 of the hemostasis clip 18. It can be appreciated that in this configuration, the hemostasis clip 18 may be releasably attached to the cap 20.

As described above, FIG. 4 illustrates that the upper jaw 24 may include a plurality of teeth 30 and the lower jaw may include a plurality of teeth 28. It can be further appreciated that the plurality teeth 30 may resemble a row of teeth 30, whereby each individual tooth 30 may be aligned with one another along the curve of the upper jaw 24. Similarly, it can be appreciated that the plurality teeth 28 may resemble a row of teeth 28, whereby each individual tooth 28 may be aligned with one another along the curve of the lower jaw 22.

FIG. 4 further illustrates that one or more of the teeth 30 of the upper jaw 24 and one or more of the teeth 28 of the lower jaw 22 may be curved inwardly from the front face of the hemostasis clip 18 toward the proximal end region of the hemostasis clip 18. For example, one or more teeth 30 of the upper jaw 24 may curve inward from a distal facing surface of the upper jaw 24 toward the proximal portion of the upper jaw 24, while one or more teeth 28 of the lower jaw 22 may curve inward from a distal facing surface of the lower jaw 22 toward the proximal portion of the lower jaw 22. It can be appreciated that, when being utilized to grasp tissue at a target tissue site, the inward curve of the one or more of the teeth 30 of the upper jaw 24 and the inward curve of the one or more teeth 28 of the lower jaw 22 may be permit the teeth 30 to grasp and pull the tissue together between the upper jaw 24 and the lower jaw 22 of the hemostasis clip 18.

It can be appreciated that after the tension member 32 is utilized to actuate the hemostasis clip 18 to grasp tissue of a target tissue site (as descried above), it may be desirable to detach the tension member 32 from the upper jaw 24 of the hemostasis clip 18 such that the hemostasis clip 18 may be left clamping the target tissue until the target tissue is occluded (e.g., the bleeding stops). Accordingly, FIGS. 5-6 illustrate two example configurations in which the shear member 34 may be utilized to detach the tension member 32 from the upper jaw 24 of the hemostasis clip 18.

Figure 5:
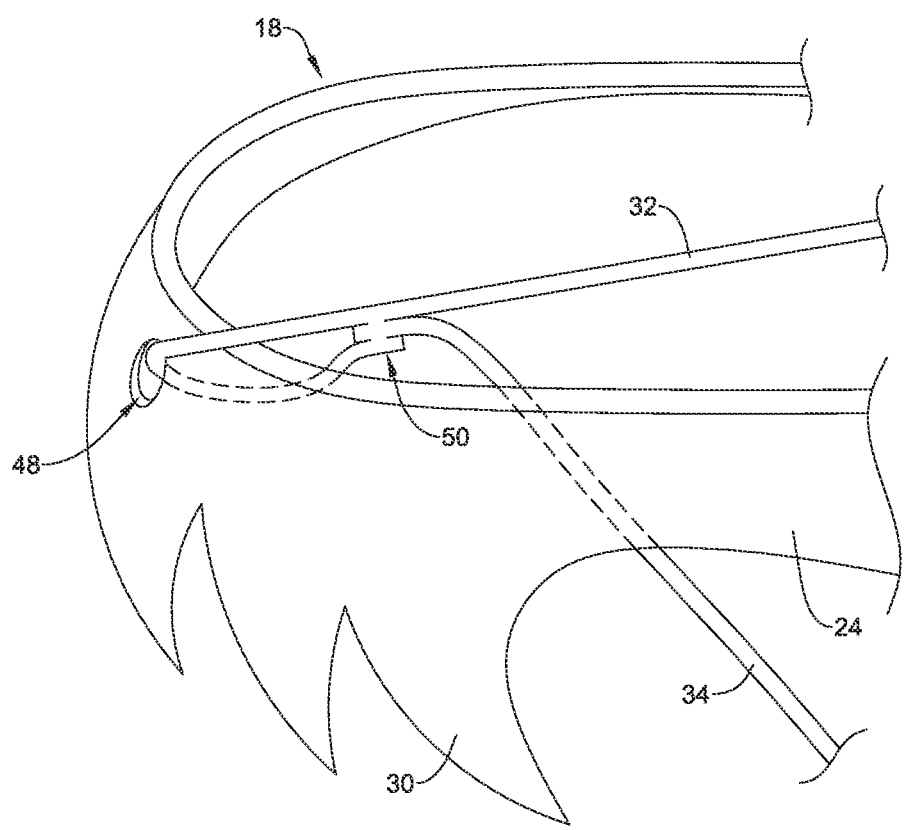
FIG. 5 illustrates a portion of another example hemostasis clip delivery system.
Figure 6:
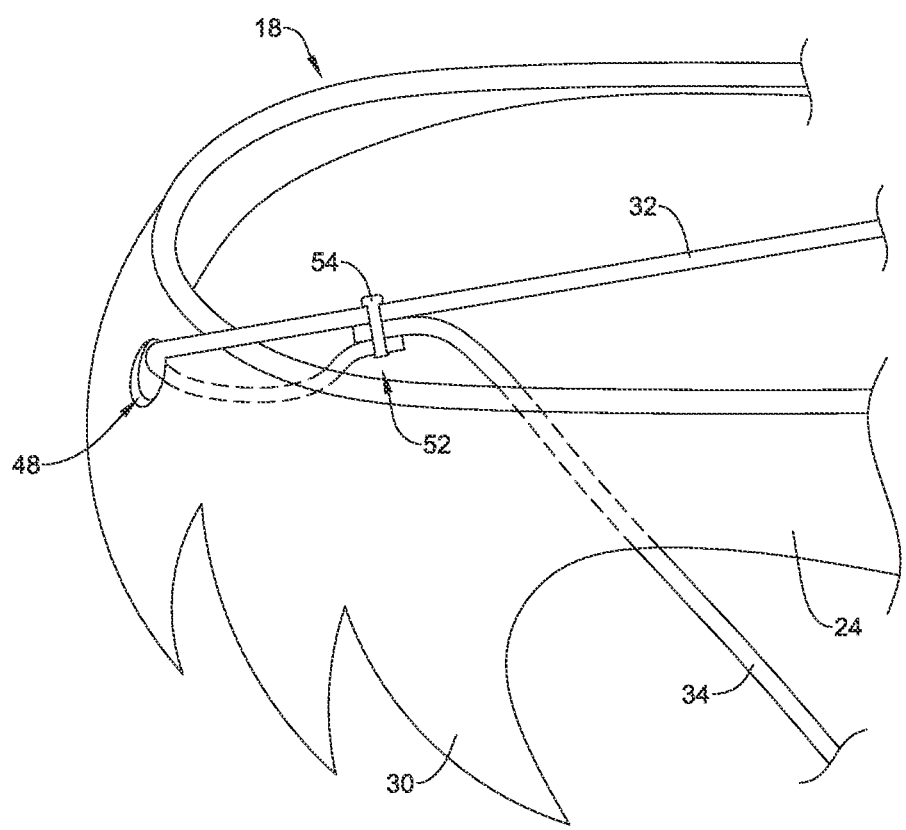
FIG. 6 illustrates a portion of another example hemostasis clip delivery system.

FIG. 5 illustrates an example configuration in which the shear member 34 may be utilized to detach the tension member 32 from the upper jaw 24 of the hemostasis clip 18. FIG. 5 illustrates that, in some examples, the tension member 32 may initially be wrapped through an aperture 48 located in the upper jaw 24. For example, FIG. 5 illustrates that the tension member 32 may be wrapped over a top surface (e.g., the upper surface) of the upper jaw 24, through the aperture 48 and extend proximally toward the proximal end region of the upper jaw 24. Additionally, referring to FIG. 2 and FIG. 5, the shear member 34 may extend from the lumen 38 of the actuation sheath 16, around the first projection 26 and behind the upper jaw 24, whereby the distal end of the shear member 34 may be secured between the distal end of the tension member 32 and a proximal portion of the tension member 32. It can be appreciated from FIG. 5 that the distal end of the shear member 34, the distal end of the tension member 32 and a proximal portion of the tension member 32 may be welded together to form a welded connection 50.

It can be appreciated that after the hemostasis clip 18 has been actuated to initially grasp tissue of a target tissue site (e.g., the hemostasis clip 18 has been opened and closed to grasp tissue of a target tissue site via manipulation of the tension member 32) the hemostasis clip 18 may be reopened (via manipulation of the tension member 32) to regrasp the tissue of the tissue target site. For example, in some instances, a clinician may initially utilize the medical device 10 to attach the hemostasis clip 18 to tissue of a target tissue site. However, in some instances, the initial grasping of the tissue may be unsatisfactory. Therefore, the clinician may desire to reposition the hemostasis clip 18 along the target tissue site. Accordingly, the clinician may manipulate the control member 12 to actuate the hemostasis clip 18 (via manipulation of the tension member 32) and regrasp the tissue. The re-grasping of the tissue may be performed repeatedly by the clinician until the appropriate amount of tissue has been positioned between the upper jaw 24 and the lower jaw 22 of the hemostasis clip 18 is achieved.

It can further be appreciated that after the hemostasis clip 18 has been actuated to grasp tissue of a target tissue site (e.g., the hemostasis clip 18 has been opened and closed to grasp tissue of a target tissue site via manipulation of the tension member 32), the shear member 34 may be translated in a distal-to-proximal direction while tension is applied to the tension member 32, thereby shearing (e.g., splitting, breaking, severing, etc.) the welded connection 50. In some examples, one or more actuation members of the control member 12 may be utilized to apply an appropriate amount of tension to the tension member 32 while also pulling the shear member 34 in a distal-to-proximal direction to break the welded connection 50.

It can be further appreciated that shearing the welded connection 50 may permit the distal end of the tension member 32 to be retracted through the aperture 48, thereby freeing the tension member 32 and the shear member 34 from the upper jaw 24. However, it is noted that the welded connection 50 may be designed such that it is strong enough to permit the tension member 32 to rotate the upper jaw 24 relative to the lower jaw 22 (prior to breaking the welded connection 50), as described above.

FIG. 6 illustrates another example configuration in which the shear member 34 may be utilized to detach the tension member 32 from the upper jaw 24 of the hemostasis clip 18. FIG. 6 illustrates that, in some examples, the tension member 32 may initially be positioned (e.g., wrapped) through an aperture 48 located in the upper jaw 24. For example, FIG. 6 illustrates that the tension member 32 may be wrapped over a top surface (e.g., the upper surface) of the upper jaw 24, through the aperture 48 and extend proximally toward the proximal end region of the upper jaw 24. Additionally, referring to FIG. 2 and FIG. 6, the shear member 34 may extend from the lumen 38 of the actuation sheath 16, around the first projection 26 and behind the upper jaw 24, whereby the distal end of the shear member 34 may be secured between the distal end of the tension member 32 and a proximal portion of the tension member 32. It can be appreciated from FIG. 6 that the distal end of the shear member 34, the distal end of the tension member 32 and a proximal portion of the tension member 32 may be coupled together via a rivet 54 to form a riveted connection 52.

It can further be appreciated that after the hemostasis clip 18 has been actuated to grasp tissue of a target tissue site (e.g., the hemostasis clip 18 has been opened and closed to grasp tissue of a target tissue site via manipulation of the tension member 32), the shear member 34 may be translated in a distal-to-proximal direction while tension is applied to the tension member 32, thereby shearing (e.g., splitting, breaking, severing, etc.) the rivet 54 of the riveted connection 52. In some examples, one or more actuation members of the control member 12 may be utilized to apply an appropriate amount of tension to the tension member 32 while also pulling the shear member 34 in a distal-to-proximal direction to break the rivet 54 of the riveted connection 52.

It can be further appreciated that breaking the rivet 54 of the riveted connection 52 may permit the distal end of the tension member 32 to be retracted through the aperture 48, thereby freeing the tension member 32 and the shear member 34 from the upper jaw 24. However, it is noted that the riveted connection 52 may be designed such that it is strong enough to permit the tension member 32 to rotate the upper jaw 24 relative to the lower jaw 22 (prior to breaking the riveted connection 52), as described above.

Figure 7:
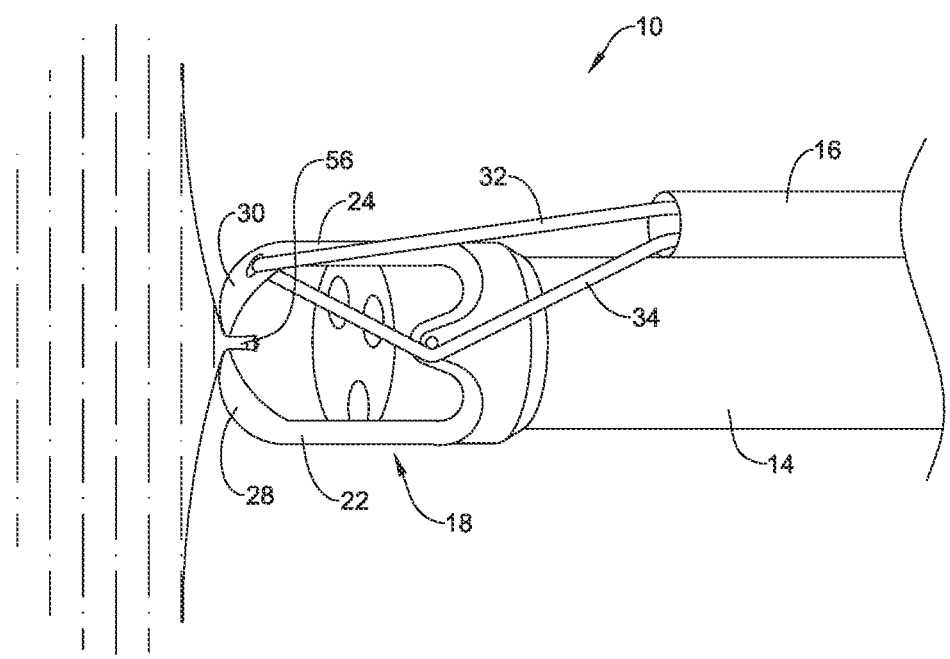
FIG. 7 illustrates an example hemostasis clip attached to a target site.
Figure 8:
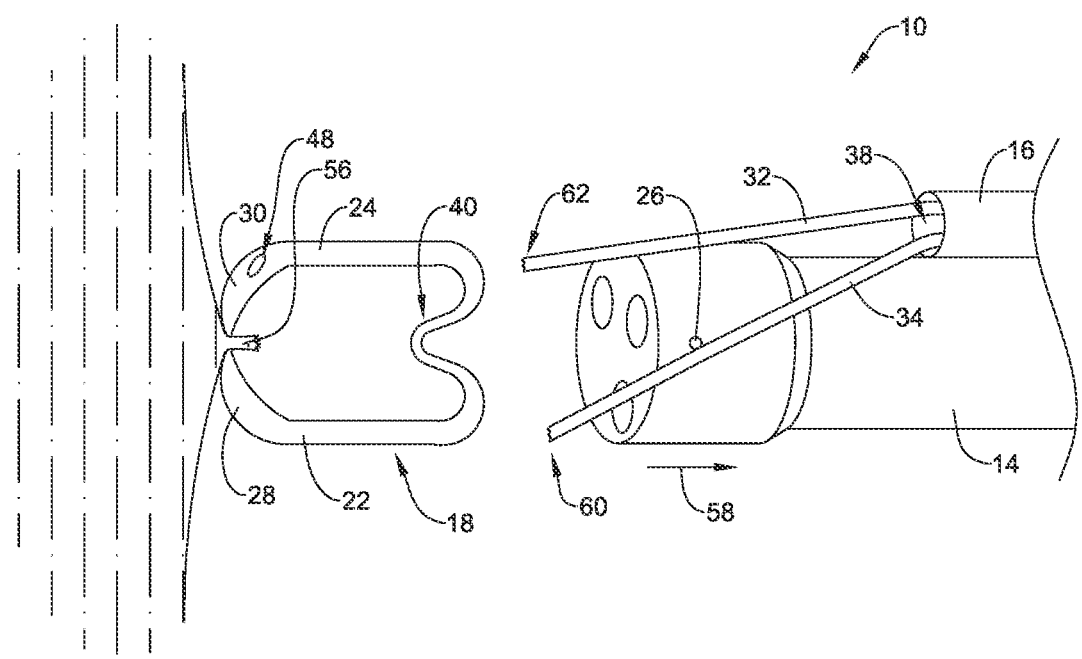
FIG. 8 illustrates an example hemostasis clip attached to a target site.

FIG. 7-8 illustrate the medical device being utilized to attach the hemostasis clip 18 to a target tissue site, as described above. It can be appreciated from FIG. 7 that the tension member 32 has been utilized to actuate the hemostasis clip 18 from a first (e.g., closed position as shown in FIG. 2), to a second position (e.g., an open position as shown in FIG. 3), and back to the first position after the shaft 14 of the medical device 10 was advanced toward the tissue 56 such that closing the hemostasis clip 18 captures the target tissue between the teeth 30 of the upper jaw 24 and the teeth 28 of the lower jaw 22. As described above, the hemostasis clip 18 may be repeatedly actuated to grasp and re-grasp tissue until the desired amount of tissue has been captured.

FIG. 8 illustrates that, after the desired amount of target tissue has been captured between the teeth 30 of the upper jaw 24 and the teeth 28 of the lower jaw 22 of the hemostasis clip 18, the shear member 34 may be retracted through the lumen 38 of the actuation sheath 16 while tension is maintained on the tension member 32. As described above, retracting the shear member 34 in a distal-to-proximal direction about the first projection 26 may shear (e.g., break) the connection between the tension member 32 and the shear member 34. It can be appreciated that the tension member 32 and the shear member 34 may be connected to one another via the welded connection 50 or the riveted connection 52 described above. It is further noted that this is not intended to be limiting. Other connection configurations are contemplated between the tension member 32 and the shear member 34.

FIG. 8 further illustrates that after the connection between the tension member 32 and the shear member 34 is broken, the distal end 62 of the tension member 32 may pass through the aperture 48, thereby freeing the tension member 32 from the hemostasis clip 18. Additionally, FIG. 8 illustrates the distal end 60 of the shear member 34 free of the hemostasis clip 18. Accordingly, it can be appreciated that a clinician may withdraw the shaft 14 (including the cap 20) from the hemostasis clip 18, thereby releasing the hemostasis clip 18 from the cap 20. Withdrawal of the shaft 14 relative to the hemostasis clip 18 is depicted by the arrow 58 in FIG. 8. It can be appreciated that the medical device 10 (including the shaft 14, the cap 20, the actuation sheath 16, the tension member 32 and the shear member 34) may be withdrawn from the body while the hemostasis clip 18 remains attached to the target tissue site 56.

FIG. 9 illustrates a top view of another example medical device 100. The medical device 100 may be similar in form and function to the medical device 10 described above. For example, the medical device 100 may include a hemostasis clip 118 (like the hemostasis clip 18) positioned on an outer surface of a shaft 114. Additionally, the medical device 100 may include a cap 120 similar to the cap 20 described above with respect to the medical device 10.

FIG. 9 further illustrates that the medical device 100 may include a tension member 132 extending through the actuation sheath 116 (positioned on an upper portion of the shaft 114). FIG. 9 further illustrates that the tension member 132 may include a first tension arm 133 coupled to an upper jaw 124 at a first weld connection 144. Additionally, FIG. 9 illustrates that the tension member 132 may include a second tension arm 135 coupled to the upper jaw 124 at a second weld connection 145.

Additionally, FIG. 9 illustrates that the medical device 100 may further include a first shear member 134 and a second shear member 136. Further, the first shear member 134 may extend out of the actuation sheath 116, around a first projection 126 (extending away from the outer surface of the shaft 14) and couple to the upper jaw 124 and/or the first tension arm 133 at the first weld connection 144. Additionally, the second shear member 136 may extend out of the actuation sheath 116, around a second projection 127 (extending away from the outer surface of the shaft 14) and couple to the upper jaw 124 and/or the second tension arm 135 at the second weld connection 144.

It can be appreciated that the medical device 100 may function like to the medical device 10 described above. For example, the hemostasis clip 118 may be actuated between an opened and closed configuration via actuation of the tension member 132. However, it can be appreciated that the first tension arm 133 and the second tension arm 135 may each apply a substantially equal retraction force on the upper jaw 124 as the upper jaw is actuated. Additionally, as described above with respect to the medical device 10, the hemostasis clip 118 may be repeatedly actuated to grasp and re-grasp tissue until the desired amount of tissue has been captured.

Additionally, it can further appreciated that after the tension member 132 is manipulated to open and close the hemostasis clip 118 to grasp tissue of a target tissue site, each of the first shear member 134 and the second shear member 136 may be retracted (while tension is maintained on the tension member 132), thereby breaking the first connection weld 144 and the second connection weld 145. It can be appreciated that first connection weld 144 and the second connection weld 145 may be similar in form and function to the connection weld 50 described above.

Additionally, after the first connection weld 144 and the second connection weld 145 are broken, it can be appreciated that the medical device 100 (including the shaft 114, the actuation sheath 116, the tension member 132, the first shear member 134 and the second shear member 136) may be retracted (and removed from the body), while the hemostasis clip 118 remains attached to tissue of a target tissue site.

Figure 10:
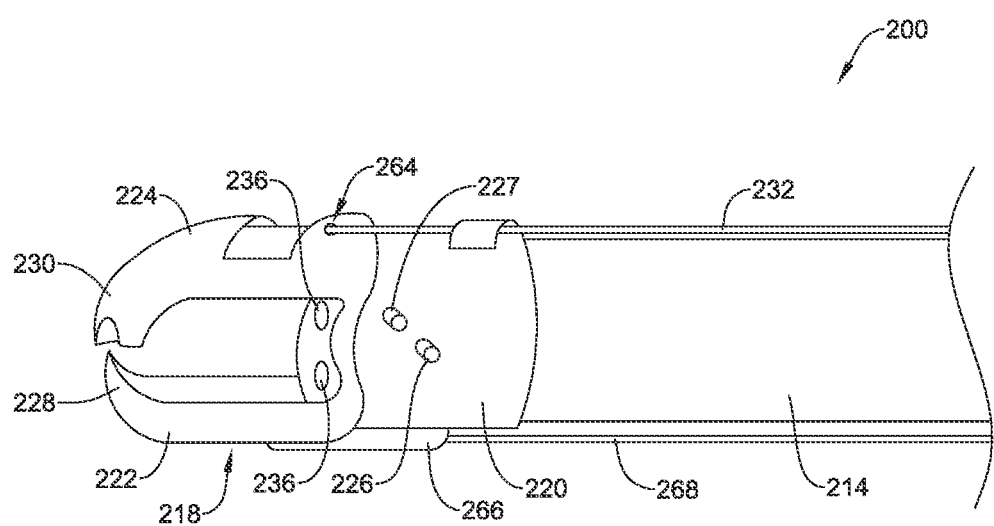
FIG. 10 illustrates another example hemostasis clip delivery system in a first position.

FIG. 10 illustrates another example medical device 200. The medical device 200 may be like other medical devices disclosed herein. For example, the medical device 200 may include a hemostasis clip 218 positioned on an outer surface of a cap 220, whereby the cap 220 is positioned on the distal end region of a shaft 214. In some examples, the shaft 214 may include an endoscope, laproscope, catheter, guide tube, or the like. As will be described in greater detail below, the distal end of the medical device 200 may be advanced within a portion of a body lumen to a position adjacent a target tissue, such as a lesion, while the proximal end of the medical device system 200 may extend out of the body lumen to a position outside the body.

As shown in FIG. 10, a one or more lumens 236 may extend through the shaft 214 from its proximal end region to its the distal end region. In some examples, one or more of the lumens 236 may be referred to as a "working channel" of the medical device 200. The working channel may be designed to permit a variety of medical devices to pass therethrough. For example, a clinician may pass or exchange a variety of medical devices through the working channel 236 over the course of a given medical procedure. The medical devices passed within the working channel 236 may be utilized to treat a tissue target site. It can further be appreciated that the reference numerals 236 may represent a working channel, while the other reference numerals may represent additional working channels of the shaft 214 or they may represent other features (e.g., LED light, water jet, camera etc.) of the shaft 214 (e.g., endoscope).

It can be further appreciated that the proximal end region of the shaft 214 may be coupled to a control member (similar to the control member 12 described above). The control member 12 may be utilized as a grip to control the translation of the shaft 214. Further, the control member may also permit a user to rotate the shaft 214. The control member may be utilized by a clinician to advance the distal end region of the shaft 214 to a position adjacent a target tissue to perform a medical treatment. Additionally, as described above, the control member 12 may include one or more actuators (e.g., knob 13), gears, levers, etc. which allow a clinician to manipulate the shaft 214 in addition to other features components of the medical device 200.

As discussed above, the medical device 200 shown in FIG. 10 may include a hemostasis clip 218 (e.g., a defect closure device) positioned on a cap 220 positioned on the distal end region of the shaft 214 (e.g., endoscope). In some examples, such as the example shown in FIG. 10, the hemostasis clip 218 may be disposed along the outer surface of the cap 220. This type of hemostasis clip may be referred to as an "over-the-scope" clip as the clip 218 as it is positioned on the outer surface of the cap 220 (e.g., endoscope) or other similar medical device.

Additionally, FIG. 10 further illustrates that the hemostasis clip 218 may include an upper jaw 224 connection to a lower jaw 222. Additionally, FIG. 10 illustrates that the upper jaw 224 may include one or more teeth 230 and the lower jaw may include one or more teeth 228. In some examples, the teeth 228 of the lower jaw 222 may extend into (e.g., nest between) a gap between two of the teeth 230 of the upper jaw 224.

FIG. 10 further illustrates that the medical device 200 may include a tension member 232 which is coupled to the upper jaw 224 of the hemostasis clip 218 at a welded connection 264. Like the medical device 10 described above, the tension member 232 may be utilized to actuate the hemostasis clip 218 between a first (e.g., closed) position and a second (e.g., open) position. For example, retracting the tension member 232 in a distal-to-proximal direction may pull on the upper jaw 224, thereby rotating the upper jaw 224 relative to the lower jaw 222.

In some examples, the lower jaw 222 may be fixed relative to the upper jaw 224. For example, FIG. 11 illustrates that when the tension member 232 is retracted in a distal-to-proximal direction, the upper jaw 224 my pivot relative to a first projection 226 and a second projection 227 extending away from an outer surface of the cap 220, while the lower jaw 222 remains in a fixed position, relative to the upper jaw 224.

Figure 11:
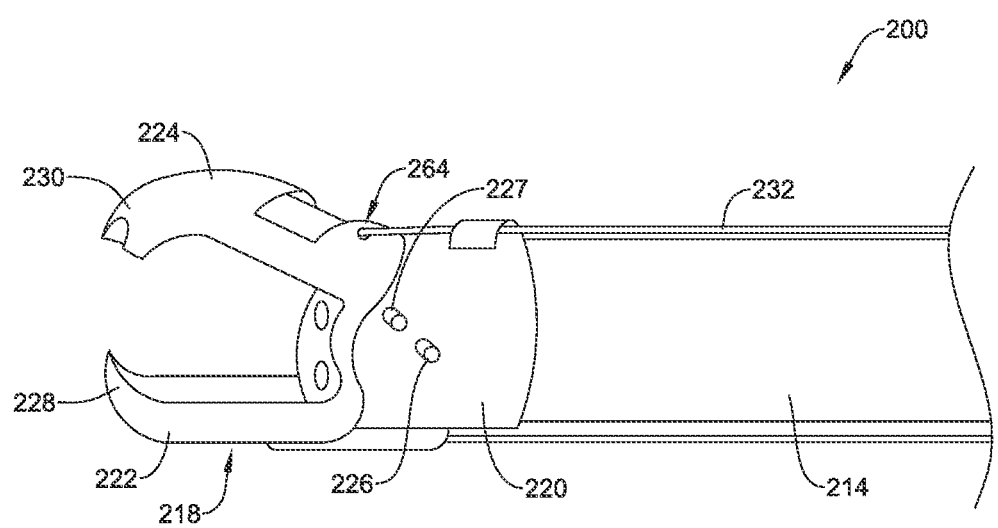
FIG. 11 illustrates the hemostasis clip shown in FIG. 10 in a second position.

As shown in FIG. 11, as the tension member 232 is retracted in a distal-to-proximal direction (via manipulation of a control member 12, for example) the upper jaw 224 may rotate away from the lower jaw 222, thereby separating the teeth 230 of the upper jaw 224 from the teeth 228 of the lower jaw 222. In this configuration, the medical device 200 may be advanced toward a tissue target site whereby the target tissue is placed between the teeth 230 of the upper jaw 224 and the teeth 228 of the lower jaw 222. When the target tissue is positioned between the upper jaw 224 and the lower jaw 222, the tension member 232 may be released (thereby releasing the retractive force imparted to the upper jaw 224), which permits the upper jaw 224 to close relative to the lower jaw 222, thereby capturing target tissue between the teeth 230 and the teeth 228. As described above, the hemostasis clip 218 may be repeatedly actuated to grasp and re-grasp tissue until the desired amount of tissue has been captured.

In some examples (such as the example medical device illustrated in FIGS. 10-11), the hemostasis clip 218 may be coupled to the cap 220 (and therefore, the shaft 214) via a connection member 266 and release member 268. Further, like the medical device 10 described above, after the target tissue has been captured by the hemostasis clip 218 (as described above), the shaft 214, cap 220 (including the connection member 266 and release member 268) and tension member 232 may be separated (e.g., retracted, released, etc.) from the hemostasis clip 218 and removed from the body. The hemostasis clip 218 may remain in the body and attached to the target tissue site.

FIGS. 12-15 illustrate the attachment and operation of the connection member 266 and the release member 268 relative to the hemostasis clip 218.

Figure 12:
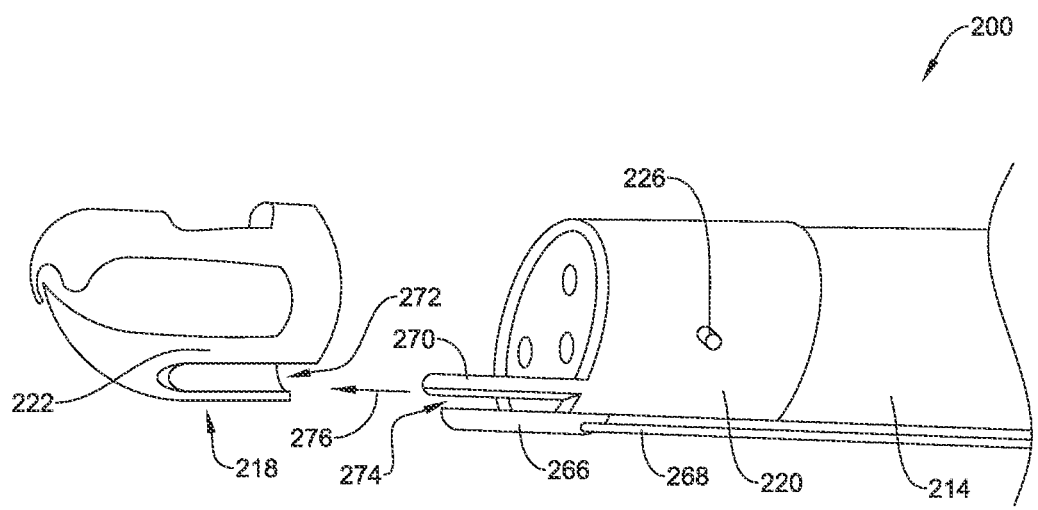
FIG. 12 illustrates another example hemostasis clip delivery system.

FIG. 12 illustrates the hemostasis clip 218 released from the cap 220 as described above. FIG. 12 further illustrates that the hemostasis clip 218 may include a slot 272 positioned along the bottom surface of the hemostasis clip 218. For example, FIG. 12 illustrates that the slot 272 may be formed within a portion of the lower jaw 222 of the hemostasis clip 218.

Further, FIG. 12 illustrates that the cap 220 may include a connection member 266 spaced away from a projection 270 (e.g., rail, stabilizer, shelf, ledge, etc.) to define an opening 274. It can be appreciated that, in some examples, the projection 270 may be vertically aligned with the connection member 266 (e.g., the projection 270 is positioned vertically above the connection member 266), whereby the shape of the projection 270 substantially mirrors the shape of the connection member 266. However, this is not intended to be limiting. Rather, it is contemplated that the projection 270 and the connection member 266 may be shaped differently from one another.

It can be further appreciated that shape of the projection 270 and the connection member 266 may be configured to mate with the shape of the slot 272 of the hemostasis clip 218. In other words, the shape of the projection 270 and the connection member 266 may be designed such that the projection 270 and the connection member 266 may be slid onto the hemostasis clip 218, whereby the wall of the hemostasis clip 218 defining the slot 272 may be inserted into the opening 274 defined between the projection 270 and the connection member 266. In other words, a portion of the hemostasis clip 218 defining the slot 272 may be sandwiched between the projection 270 and the connection member 266, thereby releasably attaching the hemostasis clip 218 to the cap 220.

It can be appreciated that, in some examples, both the projection 270 and the connection member 266 may be fixedly attached to the cap 220. In other words, in some examples, both the projection 270 and the connection member 266 may be fixed to the cap 220 such that do not move (e.g., shift, translate, etc) relative to the cap 220. In this configuration, the combination projection 270 and the connection member 266, define a fixed opening 274 which may be inserted (depicted by the reference numeral 276 in FIG. 12) into and retracted out of the slot 272, thereby releasably attaching the cap 220 to the hemostasis clip 218.

However, in other examples, the connection member 266 may be designed to translate (e.g., slide, shift, move, etc.) relative to a fixed projection 270 and the cap 220. In this configuration, translation of the connection member 266 may "release" the cap 220 from a first "locked" configuration (whereby the cap 220 is prevented from being removed from the hemostasis clip 218 until the connection member 266 is translated relative to the projection 270) to a second "unlocked" (e.g., released) configuration (whereby the cap 220 is permitted to be removed from the hemostasis clip 218 after the connection member 266 is translated relative to the projection 270).

Figure 13:
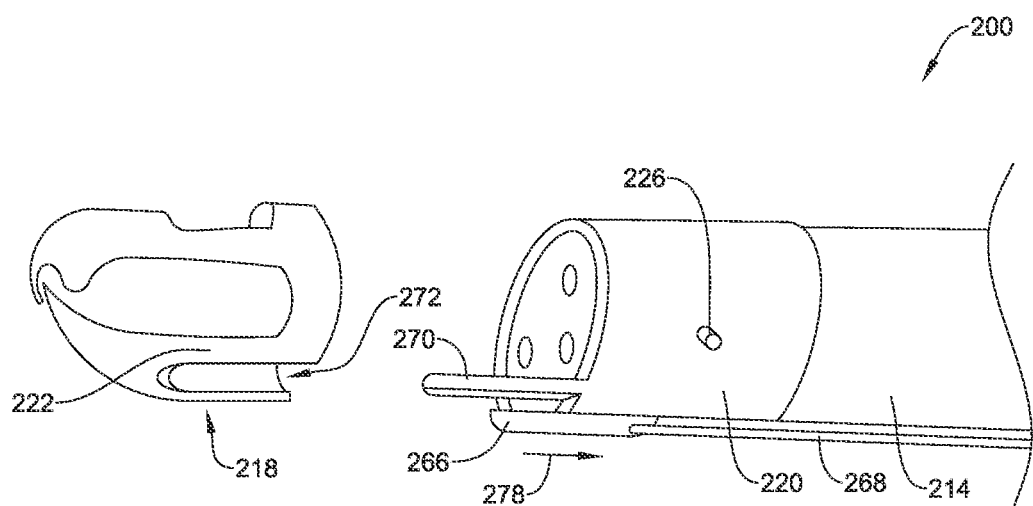
FIG. 13 illustrates another example hemostasis clip delivery system.

It can be appreciated that the translation of the connection member 266 may be accomplished by the distal-to-proximal retraction of the release member 268. For example, FIG. 13 illustrates the distal-to-proximal retraction of the release member 268 to translate the connection member 266 in a distal-to-proximal direction relative to the projection 270. As discussed above, the distal-to-proximal retraction of the connection member 266 may release the connection member 266 from the hemostasis clip 218 (e.g., shift the connection member 266 from a locked configuration to an unlocked configuration), thereby permitting the cap 220 to be proximally retracted and removed from the hemostasis clip 218.

Figure 14:
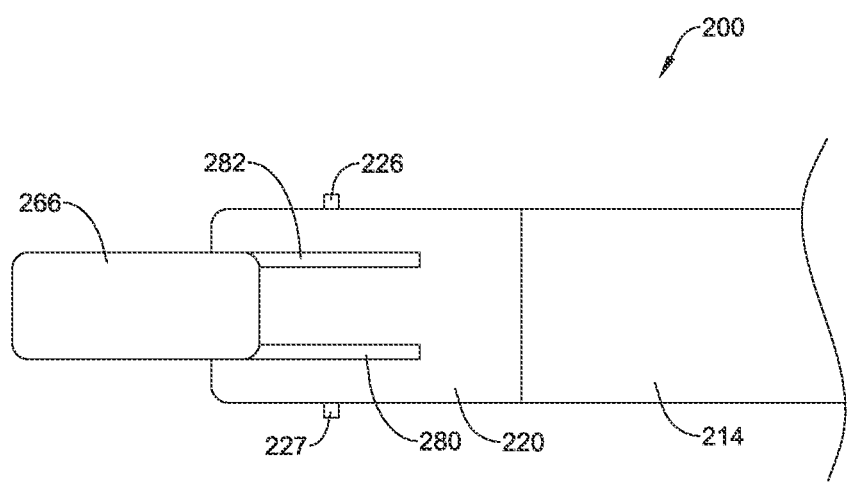
FIG. 14 illustrates a portion of an example hemostasis clip in a first position.
Figure 15:
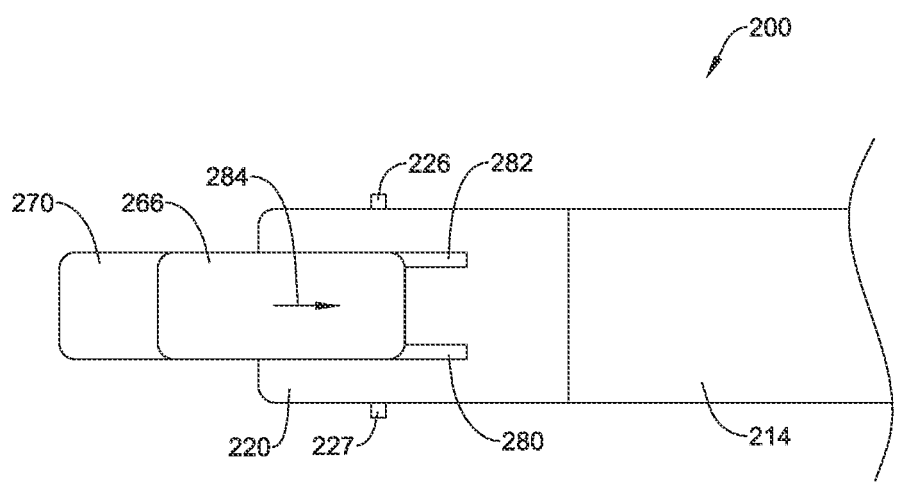
FIG. 15 illustrates a portion of an example hemostasis clip in a second position.

FIGS. 14-15 illustrate the distal-to-proximal translation of the connection member 266 described above. For example, FIG. illustrates the bottom side of the cap 220, whereby the connection member 266 is fully translated distally relative to the projection 270 (it is noted that the projection 270 is hidden by the connection member 266 in FIG. 14). In this configuration, the connection member 266 may be locked to the hemostasis clip 218 (for clarity, the hemostasis clip is not shown in FIGS. 14-15). FIG. 14 further illustrates that the connection member 266 may translate within a first longitudinal rail 280 and a second longitudinal rail 282 positioned along the bottom of the cap 220.

FIG. 15 illustrate the distal-to-proximal translation of the connection member 266 (via the distal-to-proximal retraction of the release member 268, as described above). FIG. 15 illustrates that the distal-to-proximal translation of the connection member 266 along the first longitudinal rail 280 and the second longitudinal rail 282 may shift the connection member 266 from a locked configuration to an unlocked configuration, thereby permitting the connection member 266 to be released from the hemostasis clip 218, as described above. As shown FIG. 15, the distal-to-proximal translation of the connection member 266 reveals the fixed projection 270 positioned above the connection member 266.

The materials that can be used for the various components of the medical device 10 and the various other medical devices disclosed herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 and the various other medical devices disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 and the various other medical devices disclosed herein in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 and the various other medical devices disclosed herein to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
   a shaft having a proximal end region, a distal end region and an outer circumferential surface;
   a hemostasis clip coupled to the outer circumferential surface of the distal end region of the shaft at a location proximal of a distalmost end of the shaft, wherein the hemostasis clip is configured to shift between an open position and a closed position;
   a tension member coupled to the hemostasis clip;
   wherein actuation of the tension member shifts the hemostasis clip between the open position and the closed position.

2. The medical device of claim 1, wherein the hemostasis clip includes an upper jaw pivotable to a lower jaw, and wherein the tension member is coupled to a portion of the upper jaw.

3. The medical device system of claim 2, wherein the upper jaw includes an aperture, and wherein the tension member extends through the aperture.

4. The medical device of claim 3, further comprising a shear member, and wherein the shear member is coupled to the upper jaw, the tension member, or both the upper jaw and the tension member.

5. The medical device of claim 4, wherein the shear member is coupled to the tension member at a welded connection, and wherein moving the shear member relative to the tension member severs the welded connection to separate the tension member from the shear member.

6. The medical device of claim 4, wherein a rivet couples the shear member to the tension member, and wherein moving the shear member relative to the tension member severs the rivet to separate the tension member from the shear member.

7. The medical device of claim 2, wherein the lower jaw is held in fixed position relative to the upper jaw as the upper jaw is pivoted relative to the lower jaw.

8. The medical device of claim 2, further comprising a cap disposed along the distal end region of the shaft, and wherein the hemostasis clip is releasably attached to an outer surface of the cap.

9. The medical device of claim 8, wherein the cap includes a first projection, and wherein the hemostasis clip includes a curved portion configured to engage the first projection.

10. The medical device of claim 9, wherein a portion of the shear member engages a portion of the first projection.

11. The medical device of claim 8, wherein the cap includes a connection member configured to translate from a first position to a second position, and wherein shifting the connection member from the first position to the second position releases the hemostasis clip from the cap.

12. The medical device of claim 11, further comprising a release member coupled to the connection member, and wherein retracting the release member translates the connection member from the first position to the second position.

13. An endoscope, comprising:
a handle;
a shaft coupled to the handle, the shaft having a proximal end region, a distal end region and an outer surface;
a cap disposed along the distal end region of the shaft;
a hemostasis clip releasably attached to an outer circumferential surface of the cap, wherein the hemostasis clip is configured to shift between an open position and a closed position;
a tension member coupled to the hemostasis clip;
wherein actuation of the tension member shifts the hemostasis clip between the open position and the closed position.

14. The medical device of claim 13, wherein the hemostasis clip includes an upper jaw pivotable to a lower jaw, and wherein the tension member is coupled to a portion of the upper jaw.

15. The medical device system of claim 14, wherein the upper jaw includes an aperture, and wherein the tension member extends through the aperture.

16. The medical device of claim 15, further comprising a shear member, and wherein the shear member is coupled to the upper jaw, the tension member, or both the upper jaw and the tension member.

17. The medical device of claim 14, wherein the lower jaw is held in fixed position relative to the upper jaw as the upper jaw is rotated relative to the lower jaw.

18. The medical device of claim 13, wherein the cap includes a first projection, and wherein the hemostasis clip includes a curved portion configured to engage the first projection.

19. The medical device of claim 18, wherein the upper jaw pivots relative to the lower jaw about the first projection.

20. A method of attaching a hemostasis clip to a target tissue, the method comprising:
advancing an endoscope to the target tissue, the endoscope including:
a shaft having a proximal end region, a distal end region and an outer surface;
a hemostasis clip coupled to the outer surface of the distal end region of the shaft, wherein the hemostasis clip is configured to shift between an open position and a closed position; and
a tension member coupled to the hemostasis clip;
retracting the tension member to shift the hemostasis clip to the open position;
engaging the hemostasis clip with the target tissue; and
releasing the tension member to shift the hemostasis clip to the closed position.

* * * * *